United States Patent [19]

Platt et al.

[11] Patent Number: 5,123,419
[45] Date of Patent: Jun. 23, 1992

[54] COMBINED PACEMAKER PARAMETER AND VITAL SIGN MONITOR AND METHOD OF DISPLAY

[75] Inventors: Harry L. Platt, Maroubra; Bruce R. Satchwell, West Pennant Hills, both of Australia

[73] Assignee: Micromedical Industries PTY Limited, New South Wales, Australia

[21] Appl. No.: 455,414

[22] PCT Filed: Jun. 30, 1988

[86] PCT No.: PCT/AU88/00224
§ 371 Date: Feb. 28, 1990
§ 102(e) Date: Feb. 28, 1990

[87] PCT Pub. No.: WO89/00061
PCT Pub. Date: Jan. 12, 1989

[30] Foreign Application Priority Data

Jun. 30, 1987 [AU] Australia .................. PI2805

[51] Int. Cl.⁵ ............................................. A61B 5/044
[52] U.S. Cl. ............................... 128/697; 128/419 PT
[58] Field of Search ..................... 128/697, 419 PT

[56] References Cited

U.S. PATENT DOCUMENTS

| | | | |
|---|---|---|---|
| 3,782,367 | 1/1974 | Hochberg et al. | 128/697 |
| 4,041,954 | 8/1977 | Ohara | 128/697 |
| 4,142,533 | 3/1979 | Brownlee et al. | 128/419 PT |
| 4,156,430 | 5/1979 | King et al. | 128/419 PT |
| 4,248,241 | 2/1981 | Tacchi | 128/903 |
| 4,432,360 | 2/1984 | Mumford et al. | 128/419 PG |

OTHER PUBLICATIONS

Bedini et al, "I.E.E.E. Transactions on Biomedical Engineering", vol. BME 29, No. 3, Mar. 1982, pp. 209-213.

Primary Examiner—William E. Kamm
Attorney, Agent, or Firm—Jones, Tullar & Cooper

[57] ABSTRACT

A portable combined pacemaker parameter and vital sign monitor acquires data relating to a patient's ECG waveform and an in vivo pacemaker waveform by means of electrodes which contact the patients's skin near the location of the patient's pacemaker. The monitor detects signals from the pacemaker and displays derived waveforms on a self-contained display screen. The monitor also includes a storage device to store data derived from the detected signals for subsequent recall and analysis. The waveform information is displayed on the monitor so as to show the relationship in time between the ECG waveform and the pacemaker waveform. The monitor is particularly useful for the portable measurement of ECG and/or pacemaker waveforms and for the ongoing analysis of the condition of a working pacemaker in vivo.

13 Claims, 12 Drawing Sheets

DISPLAY 1

FIG. 2B

DISPLAY 2

COMBINED PACEMAKER PARAMETER AND VITAL SIGN MONITOR AND METHOD OF DISPLAY

FIELD OF THE INVENTION

The present invention relates to a hand-held instrument which combines a pacemaker monitor and an ECG monitor into a single hand-held unit.

BACKGROUND OF THE INVENTION

Prior art equipment has measured pacemaker electrical pulse rate, the pulse width and in the case of dual-chamber pacemakers (which have two sources of electrical pulses) the interval between the two pulses (termed the A.V. interval). These are typically displayed as numeric information with no accompanying information concerning the patient's physiological state being measured or displayed at the same time.

The most relevant of the prior art patents/patent applications known to the applicant is Australian Patent Application AU-A 44712/85 to Purdue Research Foundation. This citation clearly discloses a portable monitor which provides ECG wave form information to a user by means of a hand held monitor which can be applied directly to the skin of the human thorax. The device of the citation, however, does not contemplate in any way the combining of ECG wave form display together with sensing and display of pacemaker wave form information.

At least a preferred embodiment of the present invention seeks to combine pacemaker parameter measurement and physiological vital signs measurement into a single portable unit. It is a further object of the preferred embodiment to display the shape of the pacing pulses which provide the doctor with further valuable information about the performance of the pacemaker and may warn of problems with the pacemaker lead which connects the pacemaker to the heart since the pacemaker pulse shape normally varies with the lead impedance.

SUMMARY OF THE INVENTION

In accordance with one aspect of the present invention there is disclosed a portable combined pacemaker parameter and vital sign monitor: said monitor comprising data acquisition means adapted to receive electrical signals available at a skin contact region; data processing means adapted to process said data; and display means integral with said monitor; said display means adapted to display vital sign information and pacemaker parameter information.

Preferably said vital sign information includes ECG waveforms, and heart-rate.

Preferably said pacemaker parameter information includes the pacing rate, the AV delay, the width of the pacing pulses and the pacemaker pulse waveform.

Preferably the pacemaker signals are picked up from the skin of the patient in which the pacemaker is implanted using conductive electrodes. The signals are then amplified and filtered and converted into digital information for analysis and display.

In a further broad form there is provided a method of displaying vital sign and pacemaker pulse information on a single display means, said method comprising:

deriving ECG wave form data from an ECG wave form occurring in a living body in real time;

deriving pacemaker pulse data from pacemaker pulses occurring in a pacemaker operating within said living body in real time;

displaying a reconstruction of said ECG wave form on said display means, superimposing upon said reconstruction of said ECG wave form timing markers showing the moment of occurrence of pacemaker pulses relative to said ECG wave forms.

Preferably said method includes processing said pacemaker pulse data to verify that said pacemaker pulses are stimulating the heart in a manner appropriate to the mode in which said pacemaker is operating.

Preferably said method further includes optionally displaying on said single display means a reconstruction of said pacemaker pulses.

DRAWINGS

Two embodiments of the present invention will now be described with reference to the drawings in which.

DETAILED DESCRIPTION OF PREFERRED EMBODIMENTS

The embodiments of the present invention have, as a common aim, the production of a portable, hand held monitor which allows the in situ monitoring of both the ECG wave forms of a patient and the wave forms produced by a pacemaker module which is installed and operational in the patient's body. The monitor of the preferred embodiments carries out these two complementary functions in a non-invasive manner and in real time.

Furthermore, a predetermined amount of data derived by the monitor is stored within the monitor for subsequent analysis or transmission to remote data processing means thereby enhancing the utility of the portable monitor.

FIRST EMBODIMENT

Figure 1:
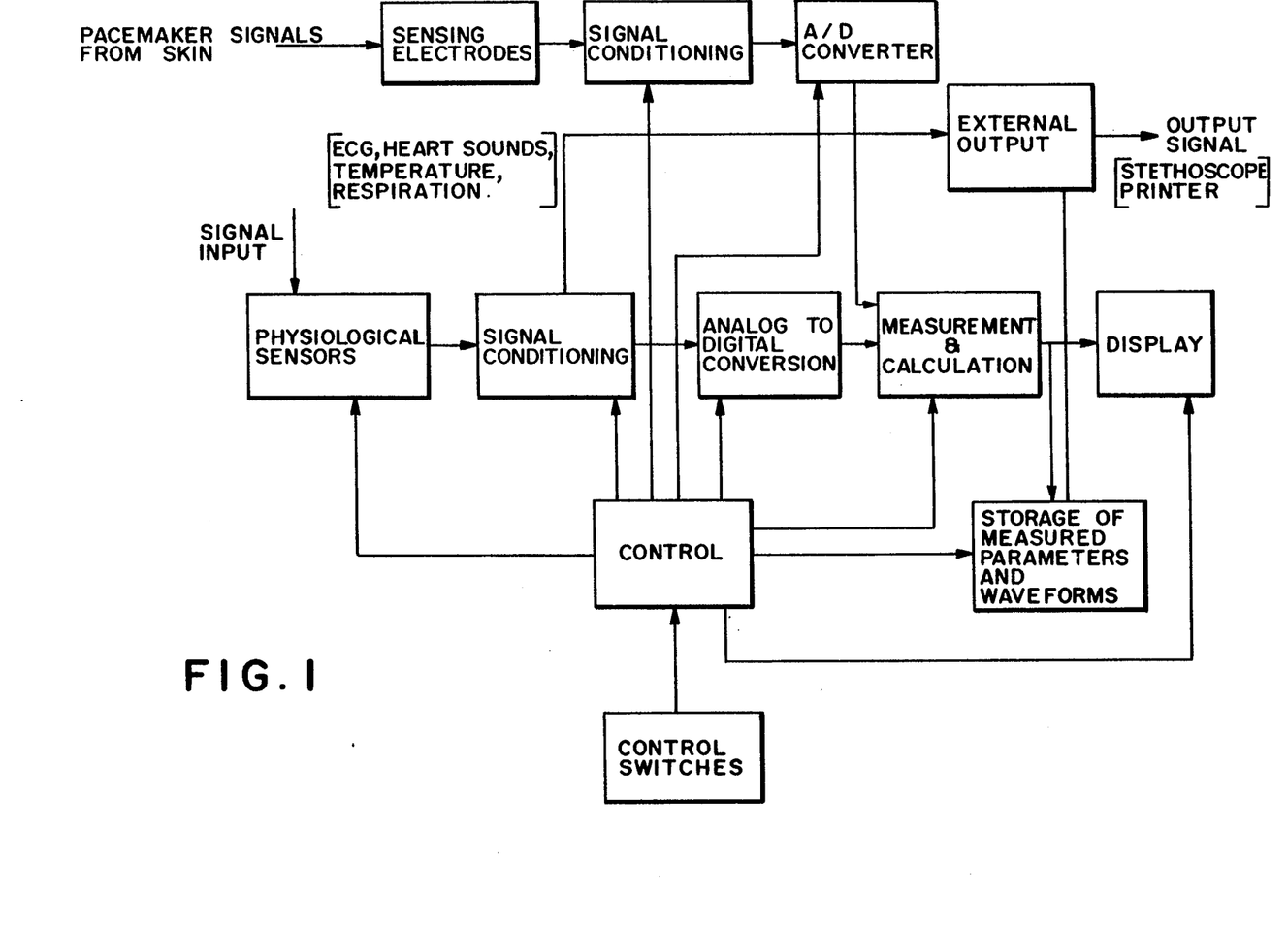
FIG. 1 is a block diagram of the monitor of a first preferred embodiment.
Figure 2A:
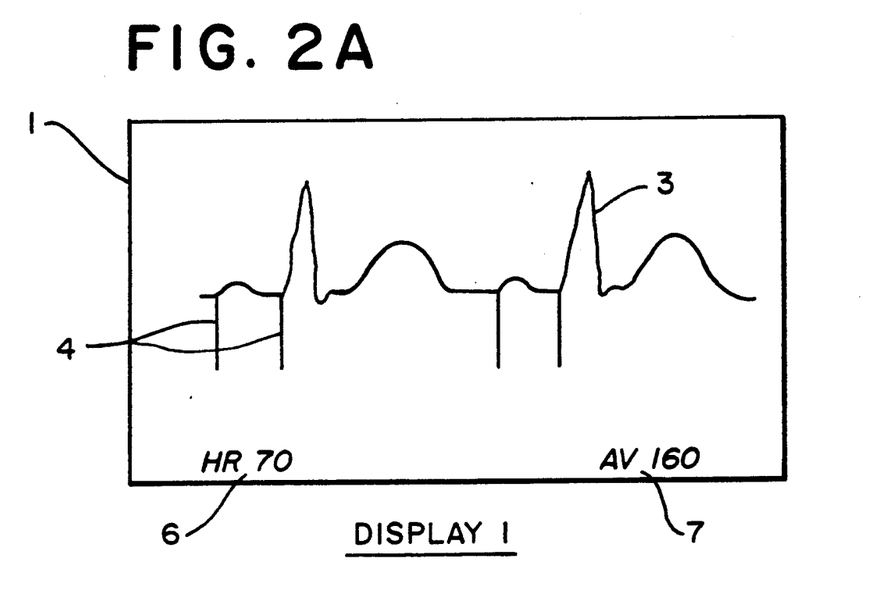
FIGS. 2A and 2B show two display formats available from the monitor of the first and second embodiment.
Figure 2B:
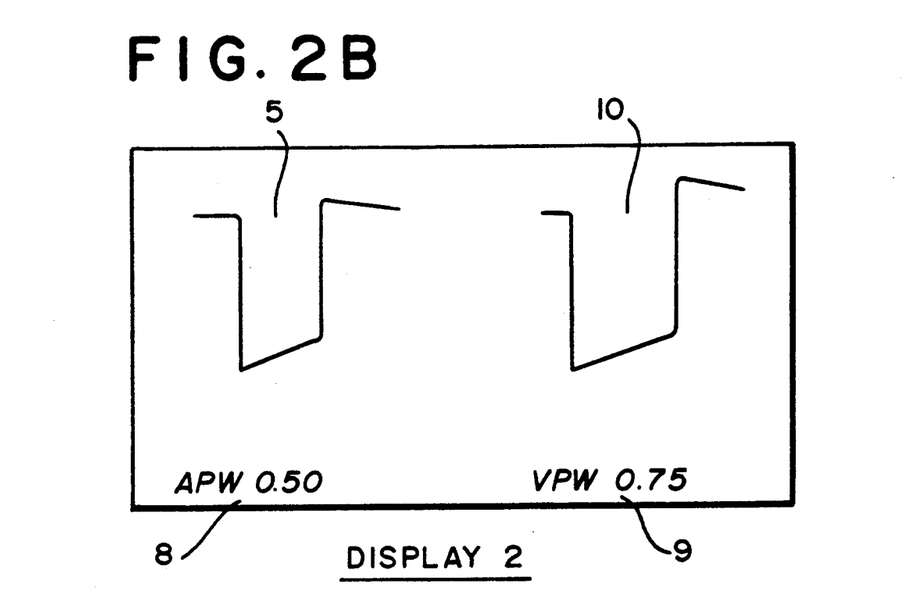

The device of the first embodiment combines all of the features disclosed in the device of copending PCT Application No. AU88/00016 (i.e. the obtaining and display of ECG information, heart sounds, temperature and respiration by means of a hand held, portable device which incorporates multi-functional electrodes) together with the deriving and display of pacemaker pulse information on the same display, the pacemaker pulse information being derived from the same multi-functional electrodes. Information for display is derived generally as shown in the block diagram of FIG. 1. The display essentially takes one of two available formats at any one time: the two formats are shown in FIG. 2. It will be noted that the screen output labelled as display 1 in FIGS. 2A and 2B shows a derived QRS wave form 3 having superimposed thereon vertical bars or timing markers 4, these bars or timing markers showing the relative position of the pacemaker pulses in time relative to the QRS wave form.

Atrial, ventricular and dual-chamber pacemakers are all able to be monitored, with accurate measurements of the pacemaker parameters clearly displayed.

The ECG is also displayed on the clear, high resolution screen to observe cardiac and pacemaker function, and ensure that reliable heart capture is occurring.

The pacing pulse waveforms 5 and 10 are also able to be displayed as shown by Display 2 and FIG. 2B, allowing observation of pulse shape to highlight any anomalies or gross changes in lead pacing impedance.

Hard copy recordings of the pacemaker parameters, ECG, and pacing pulse waveforms can be made on an optional paper strip recorder.

The preferred embodiment not only displays physiological signals but also displays measurements and waveforms relating to implanted pacemaker electrical activity. This is performed by monitoring electrical pulses on the skin which originate from the implanted pacemaker.

The first preferred embodiment of the present invention is encased in similar fashion to the portable physiological monitor disclosed in Australian Specification PH 09984 which has been subsequently published under PCT Application No. AU88/00016, the text and drawings of which are incorporated herein by cross reference.

Essentially electrical signals are derived from the skin of a patient by means of a three electrode structure or equivalent. Referring to FIG. 1 the signals from the sensing electrodes are fed to a signal conditioning unit thence converted to digital form and subsequently processed by the device according to the general block diagram of FIG. 1. The processed information is displayed as generally shown in FIGS. 2A and 2B.

Referring to FIG. 2A, information displayed, shown as Display 1, on the output display is as follows:

ECG

A waveform display of the heart's electrical activity (electrocardiogram) 3 is shown with vertical bars 4 being added to show the position of the pacemaker pulses 5 and 10 in relation to the ECG 3.

HEART RATE

Numeric information 6 showing the patient's heart rate is displayed on the screen 1 at the same time.

A.V. Delay

In the case of a "dual chamber" pacemaker which has two sources of pacing pulses, the delay between the pulse from one source to the pulse from the other is known as the A.V. Delay and is displayed as numeric information 7.

Referring to FIG. 2B, information is displayed, as on Display 2, as follows:

PACEMAKER PULSE WAVEFORM

The actual shape of the pacemaker pulses 5 and 10 are displayed to highlight any abnormalities which may be due to a fault in the pacemaker or pacemaker lead.

PACING RATE

The rate at which the pacemaker is emitting pulses to the heart can be displayed as numeric information.

PULSE WIDTHS

The width 8, 9 of the pacing pulses is displayed numerically, typically in the range 0.25 to 1 millisecond. The atrial pacing pulse width 8 is displayed separately from the ventricular pacing pulse width 9.

An example of two typical displays is shown in FIGS. 2A and 2B. The user can switch between the two displays by means of a mode control button (not shown) on the device.

Specifically in FIG. 2A, display 1, a heart rate of 70 beats per minute is shown 6 and an AV interval of 160 ms is shown 7. In display 2 of FIG. 2B an atrial pacing pulse width of 0.50 ms is shown 8 and a ventricular pacing pulse width of 0.75 ms 9 is shown.

SECOND EMBODIMENT

Figure 3:
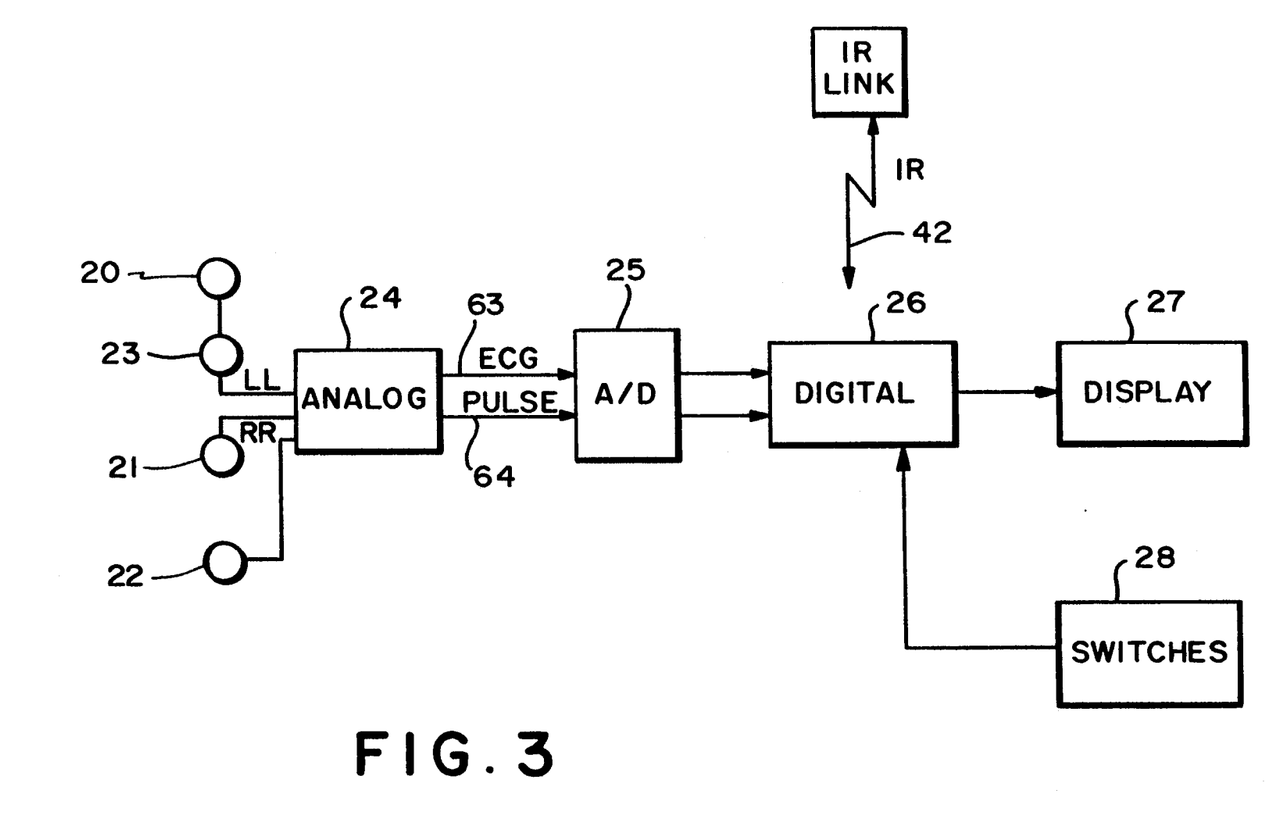
FIG. 3 shows a block diagram arrangement of a second embodiment of the invention.

The device of the second embodiment is constructed functionally according to the block diagram of FIG. 3. Four electrodes 20, 21, 22, 23 receive low level signals from a patient. The signals are initially processed by an "analog block 24", which block separates out signals associated with the ECG wave form of the patient and also (and separately) those signals associated with a cardiac pacemaker operational within the patient's body. The analog block 24 then feeds the pacemaker pulse signal 64 and the ECG signal 63 (to an analog to digital converter 25). The digital pacemaker pulse signal and the digital ECG signal are then passed to a digital processing block 26. The digital processing block 26 processes the digital pacemaker pulse signal and the digital ECG signal and displays appropriate process information on the front panel display 27 in conjunction with the operator's requirements as expressed by appropriate operation of the side mounted switches (block 28 of FIG. 3).

Figure 4:
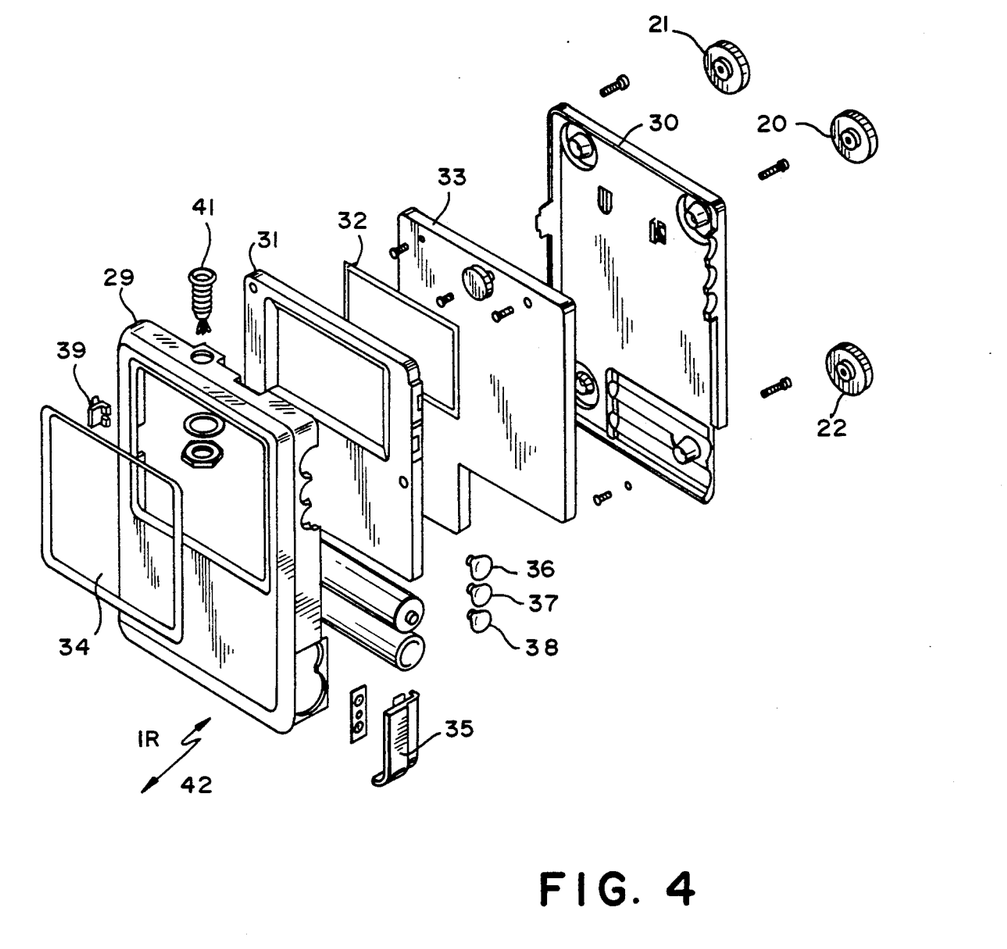
FIG. 4 shows an exploded view of the casing for the second embodiment.

FIG. 4 shows the arrangements of the casing of the second preferred embodiment. With particular reference to FIG. 4 the exploded view shows the casing to comprise a front cover 29 and a back cover 30 between which are sandwiched a liquid crystal display panel 31, a back light panel 32 and a printed circuit board 33. A display window cover 34 is applied to the front face of the front cover 29. The liquid crystal display 31 is viewed through this display window 34. The electrodes 20, 21, 22 and 23 (23 not shown) are affixed to the back cover 30 and provide the principal means of deriving ECG and pacemaker signal information from the patient when the monitor is used in portable mode. Information can also be input to the device through the patient cable connection 41. Primary controls for operating the monitor comprises on/off switch 39, "hold" push button 36, "record" push button 37 and "mode" toggle push button 38. A battery cover 35 covers the batteries once they are placed within the casing. An infrared link 42 is used to communicate data derived by the monitor to other data processing means.

The front cover is mated with the back cover in permanent fashion by use of socket screws being the same screws which hold the electrodes 21-23 to the back cover.

The LCD display used incorporates trapezoidal picture elements with a denser layout. The display sweep speed is 12.5 mm per second, the viewing area is 38.1 by 50.8 mm. The trapezoidal picture elements are arranged in a 120×480 matrix thereby comprising a total of 57,600 elements. The element itself is a TN type liquid crystal.

The electrodes 20-23 each comprise a section from a 16 mm diameter stainless steel (AISI type 316 stainless steel) rod. The working thickness of the electrodes is 3 mm.

Figure 5:
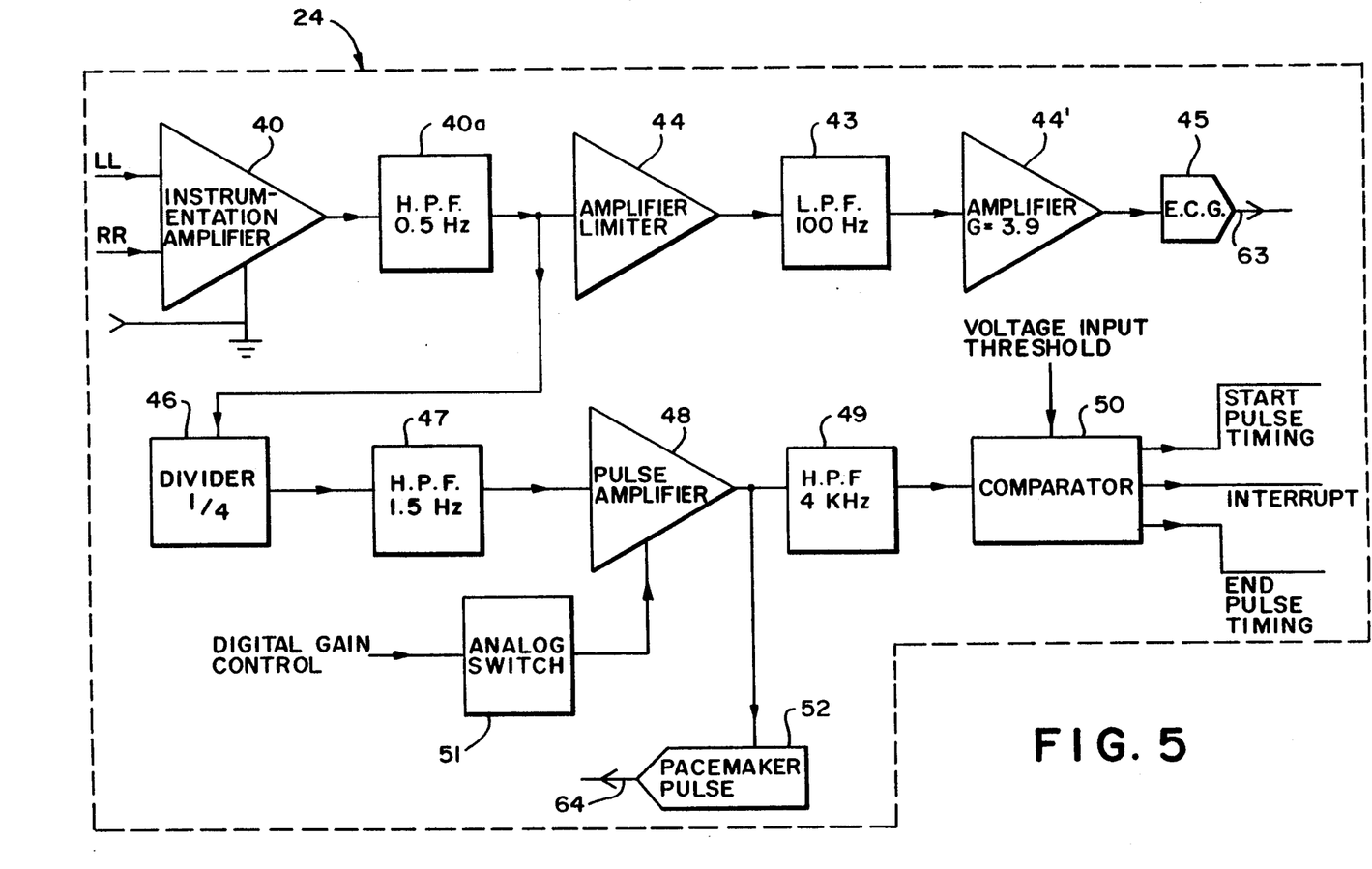
FIG. 5 is a block diagram of the functional components comprising an analog block of a third embodiment.

The electronics of the device are primarily incorporated on the one printed circuit board 33. The board incorporates the analog block 24, the analog to digital converter 25, the digital block 26 and an electronic power supply. A third embodiment of the device will now be described with reference to FIGS. 5 and 6, in which the analog block 24 is shown in greater functional detail. Functionally, FIG. 5 operates as follows:

The signals LL and RR from the skin electrodes are amplified by a factor of 10 in the instrumentation amplifier 40. It is then filtered through an 0.5 Hz high pass filter 40a to reduce base line movement on the output screen. Then the signal is split and fed to the ECG channel 45 and the pacemaker-pulse channel 52.

The first signal is amplified by 100 in amplifiers 44 and 44' and filtered with a low pass filter (LPF) 43 of 100 Hz. This output is taken to the A/D converter 25 (shown in FIG. 6 (integral within CPU 57) and used as the ECG signal 63.

The second channel signal, which is the pacemaker pulse signal from the output of the high pass filter (HPF) 40a is divided by 4 in divider 46 and is filtered by high pass filter 47. A digitally gain-controlled amplifier 48 is subsequently used to amplify the pulses for signal processing. It is controlled by the CPU 57 (shown in FIG. 6) by way of analog switch 51. The output of the amplifier provides an input 52 to the second channel 64 of the A/D converter 25 and is later displayed on the LCD screen 31. A HPF 49 of 4 KHz is used to remove low frequency skin vibrations and detect pulse edges. A constant threshold is used to differentiate between noise and pulses. A comparator 50 compares the threshold level with the pulse edges and produces a start and end of pulse timing signal. These allow the CPU to calculate the duration of the pulse. An interrupt is generated 3 ms after the beginning of pulse to start the pulse processing routine in the CPU 57.

Figure 6:
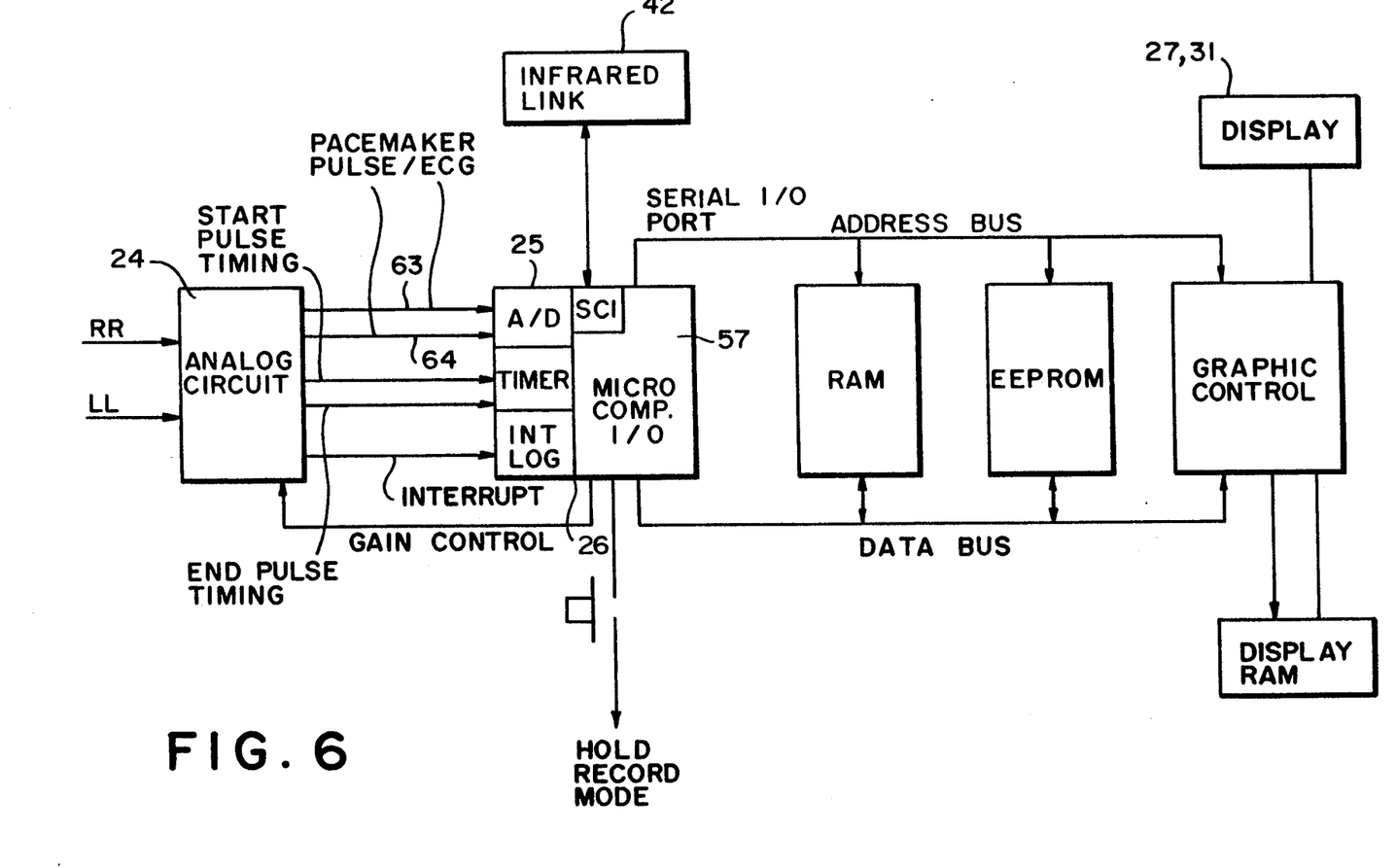
FIG. 6 shows in more detail the components comprising a third embodiment and their interconnection.

The other major functional component on the printed circuit board 33 is the digital block 26. Functionally this block is generally as shown in FIG. 6. Note that the analog to digital converter 25 (refer to FIG. 3) is, in fact, on board the microprocessor (CPU 57) on the digital block 26.

FIG. 6 shows in greater detail the components of the main printed circuit board 33 and their interconnection.

Figure 7:
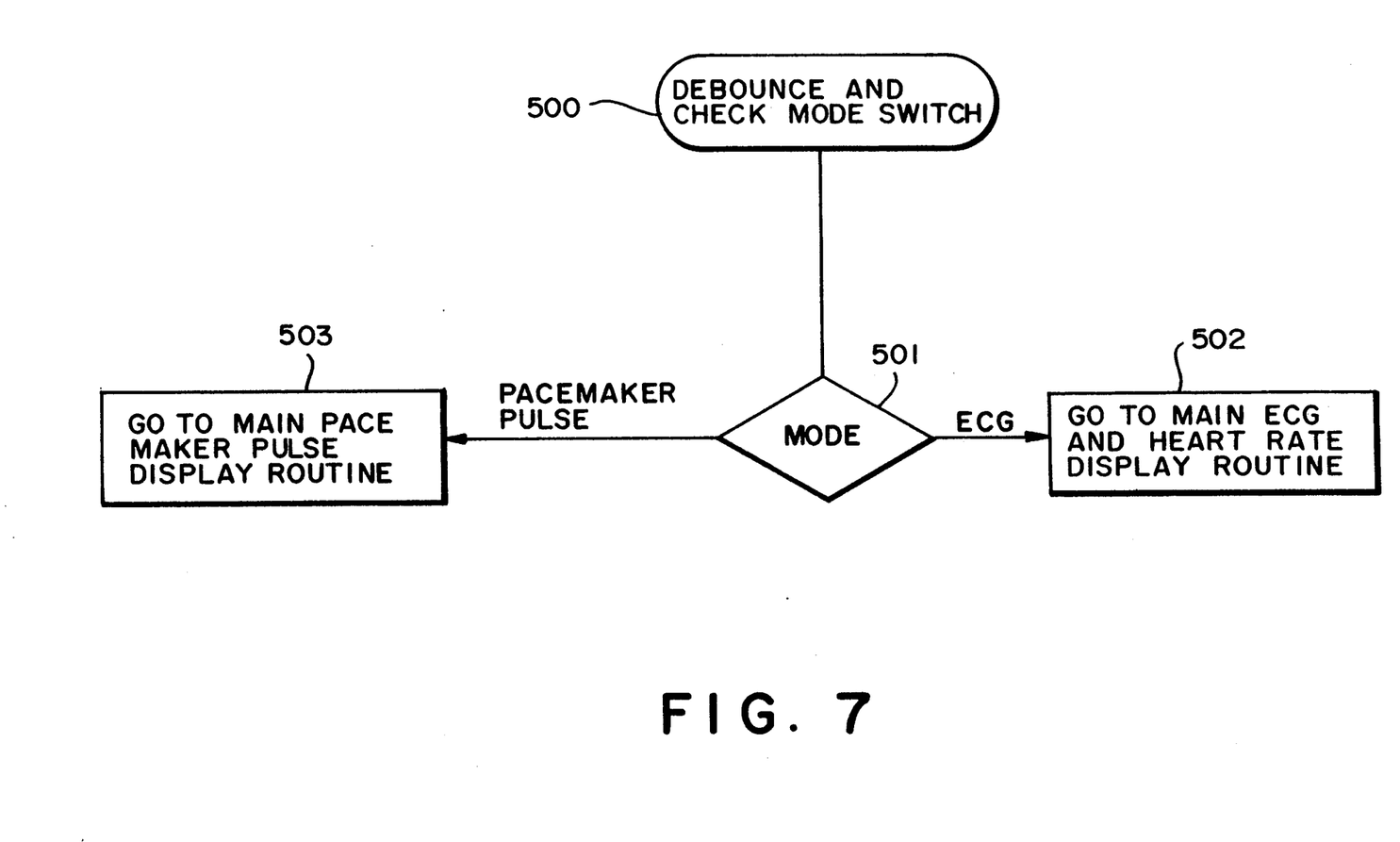
FIG. 7 is a flow chart of the mode switch interrupt service routine of the third embodiment.

The software for execution by the CPU 57 is shown in flow chart form in FIGS. 7 through to 12 inclusive.

FIG. 6 is a block diagram of the third embodiment showing its functional construction.

The analog circuit 24 is as described in FIG. 5. The outputs from the analog circuit directly connect to a single-chip microcomputer (in this embodiment the Motorola MC68HC11) 57. The ECG signal 63 and pacemaker pulse signal 64 are converted into digital form by the analog to digital converter 25. The Start and End signals from the analog circuit connect to input capture registers which capture the time at which these events occur to enable measurements of pacing pulse parameters and generation of timing markers on the ECT display. The interrupt signal is used to generate an interrupt in the microcomputer and when a pacing pulse occurs to enable execution of the appropriate software routines.

The infra-red link 42 allows transmission of acquired data and waveforms to a remote printer or computer for printout, storage or analysis. The infra-red link is connected to the Serial Communications Interface (SCI) of the microcomputer and data is transmitted using a digital serial protocol.

The microcomputer is connected to the RAM, EEPROM and Graphics Controller Chip by separate address and data buses.

The program code is stored in the EEPROM. EEPROM is used rather than ROM so that the software can easily be upgraded without needing to remove the chip from the board.

The RAM is used to hold variables during program execution, and is also used for storage of ECG and pacemaker pulse waveforms and pacemaker pulse parameters for later recall and display. The stored data may also be transmitted via the infra-red link 42 to a printer or computer.

The Graphic Controller generates the signals required to drive the display 27, 31. A bit-map of the image to be displayed is stored in the display RAM. The Graphic Controller then periodically writes this image-data to the display to enable it to be viewed. The types of images generated are shown in FIGS. 2A and 2B. The Graphics Controller is under control of the microcomputer 57.

The three control buttons for the device labelled HOLD, RECORD and MODE, are connected to input lines of the microcomputer. Button pushes are detected by the software, causing the appropriate actions to be performed.

As mentioned above, the on-chip A/D converter 25 and timer are used for sampling ECG channel 63 and pacemaker channel 64. T3 input capture registers (internal to processor) are used for detecting pacemaker spikes. In response to a detected pacemaker spike, the monitor hardware generates two pulses at the first and second input capture register inputs to mark the start and end points of the pacemaker spike. Timing information with regard to these events is then automatically stored in the first and second input capture registers. A 3 ms delayed interrupt pulse following the end of pacemaker spike is applied to the third input capture register input. This pulse sets the necessary interrupt for the service routine which then stops sampling and calculates the pulse width as the time difference between first and second input capture register contents. The 3 ms delay ensures that the complete shape of the pacemaker pulse is sampled and stored in the buffer.

When the power is first turned on (by switch 39), the program starts with the main ECG and heart rate display routine as shown in the software flow charts. The mode switch 38 is assigned to the highest priority interrupt and when pressed toggles between ECG and pacemaker pulse modes. The ECG routine consists of a main routine for displaying graphics and an interrupt service routine for sampling, filtering and QRS wave form detection. The following routines are shown in the flow charts:

main routine
   interrupt service routine
   QRS detection algorithm.

Similarly, the pacemaker pulse display consists of a main routine for continuous sampling the pacemaker channel and an interrupt service routine to stop sampling and display pulse information and shape. These routines are also shown in the flow charts.

Figure 8:
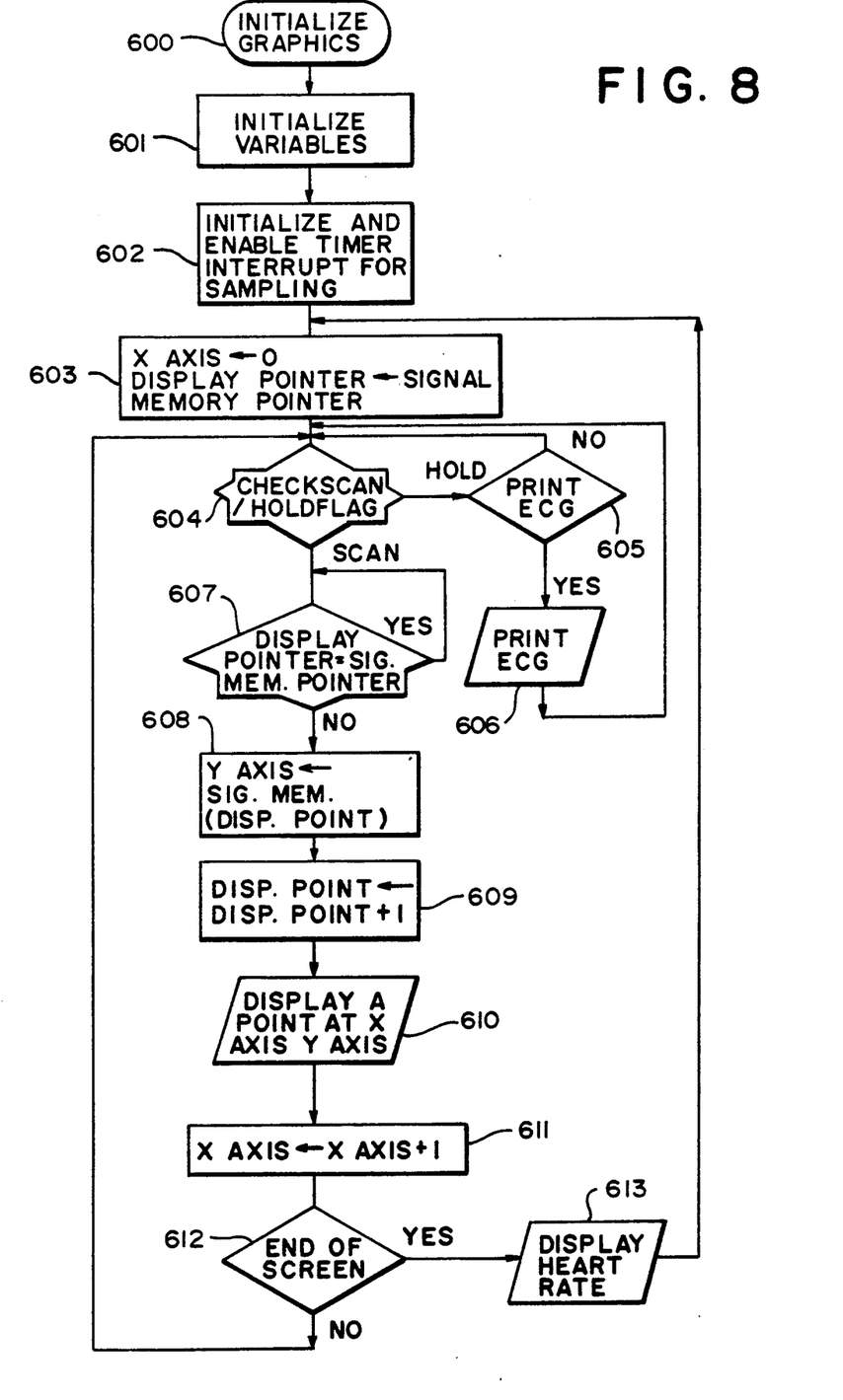
FIG. 8 is a flow chart of the main routine for ECG and heart rate display of the third embodiment.

FIG. 8 illustrates the flow chart for the mode switch interrupt service routine. This routine is activated when the mode switch 38 (FIG. 4) is depressed. In the first block 500 the switch is checked to determine that it has been pressed long enough and a debounce routine prevents multiple interrupts due to bouncing of the contacts of the switch.

In block 501 the mode is toggled to between ECG and pacemaker pulse mode with each valid mode switch activation.

Figure 9:
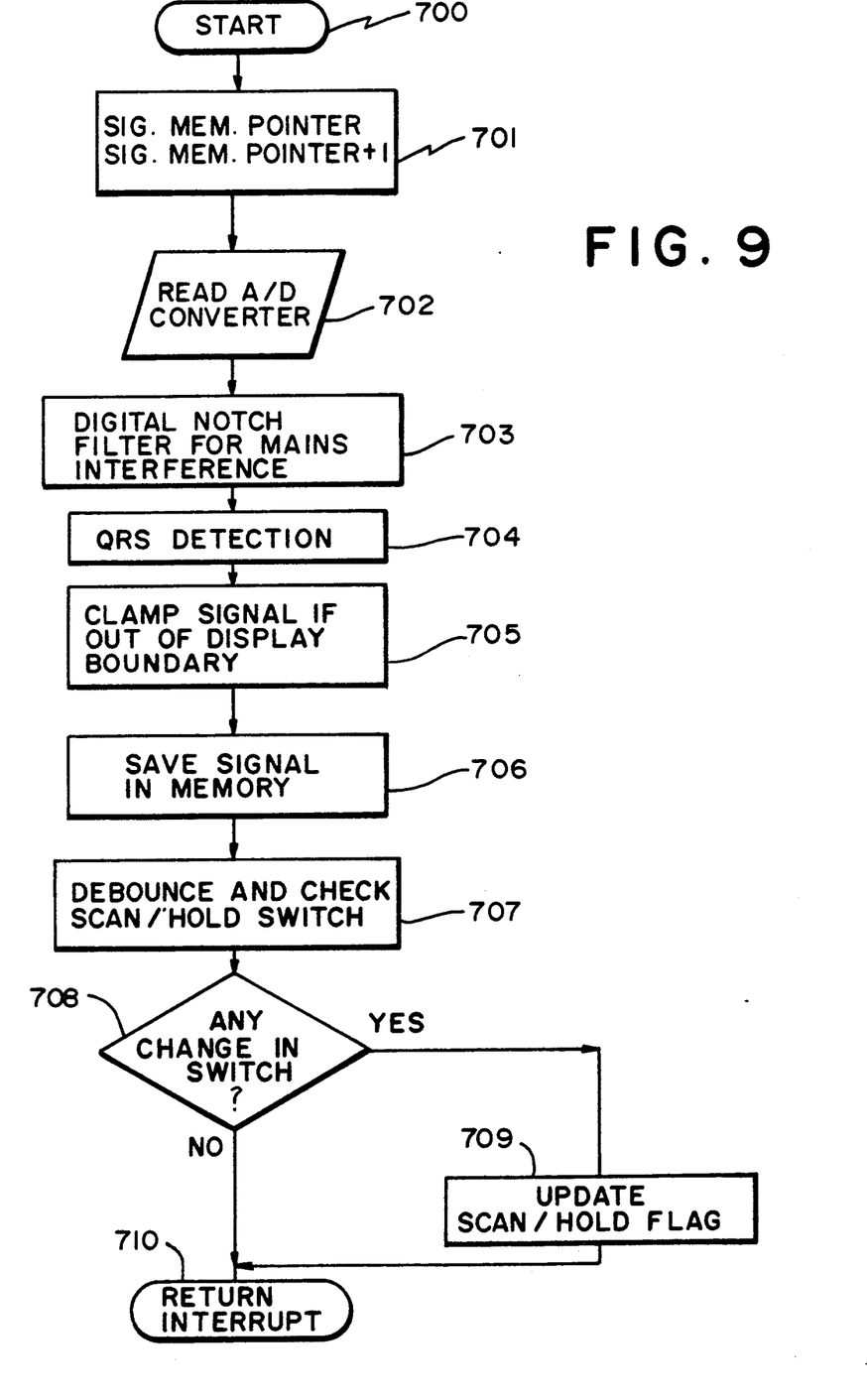
FIG. 9 is the timer interrupt service routine for the ECG and heart rate display of the third embodiment.

If ECG mode is selected, then block 502 describes the next action, which is to go to the main ECG and heart rate display routine (FIG. 9).

Figure 12:
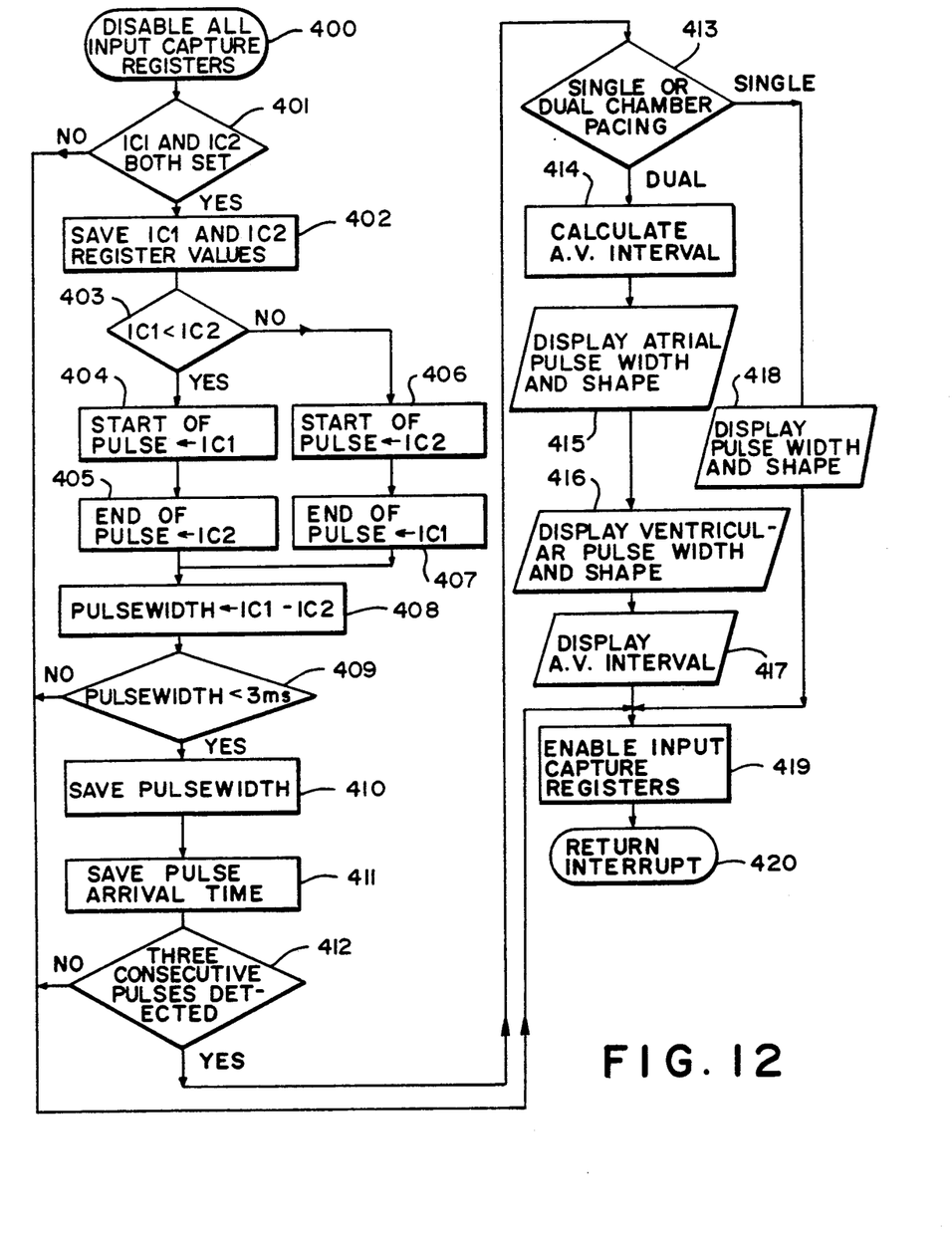
FIG. 12 is a flow chart of the pulse interrupt service routine for the pacemaker pulse display of the third embodiment.

If pacemaker pulse mode is selected then block 503 describes the next action, which is to go to the main pacemaker pulse display routine (FIG. 12).

The main routine for ECG and heart rate display is illustrated by the flowchart FIG. 9. This routine initializes the hardware and variables and then displays the ECG and heart rate on the LCD display as they are acquired.

Figure 10:
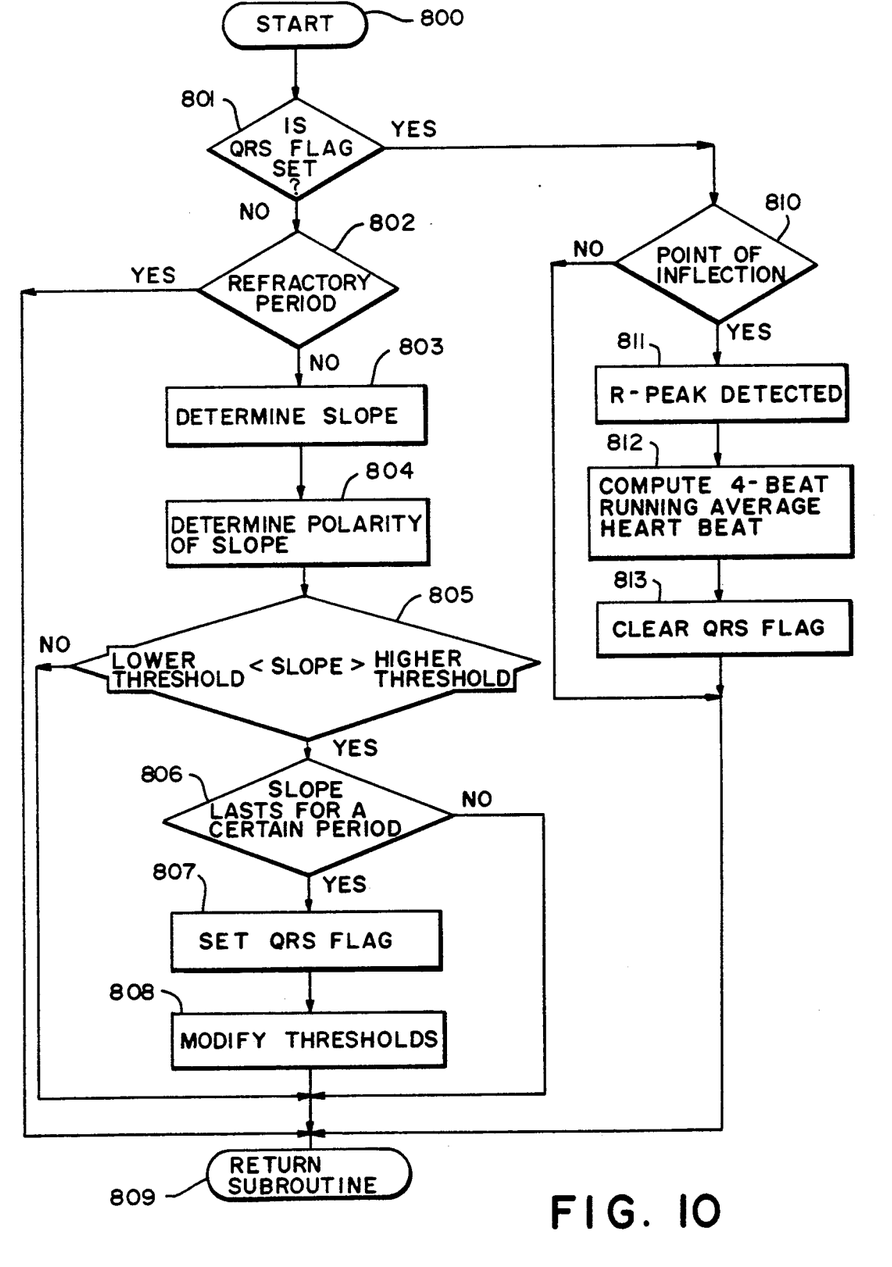
FIG. 10 is the flow chart of the QRS detection algorithm for the ECG and heart rate display of the third embodiment.

The routine starts at block 600 where the graphics are initialized; as are the variables (block 602). The timer interrupt is then initialized and enabled (block 602), which results in there being a periodic interrupt to sample the ECG. The routine for this is shown in FIG. 10.

At block 603 the X axis display coordinate is set to zero and the display pointer is set to the value of the signal memory printer.

Next, the scan/hold flag is checked (block 604) to determine if the hold switch 37 has been pushed. Hold and scan are selected alternately. If hold is selected, then at block 605 it is checked to determine whether a print of the ECG is required (determined by switch 360. If not, then block 604 is reentered. If a print of the ECG is required, then at block 606 the ECG data is output to the infra-red link 42 for transmission to a printer. Block 604 is then reentered.

If scan is selected then at block 607 the display printer is checked to see if it is equal to the signal memory printer. If not, then the Y axis display printer is set to the value in the signal memory indexed by the display printer (block 608). Then the display printer is incremented by one (block 609). A print is then written to the display determined by the X and Y axis coordinates (block 610). The X axis coordinate is then incremented by one (block 611). At block 612 it is checked if the screen boundary has been reached. If it has, then the heart rate is updated on the display (block 613) and the routine continues at block 603. If the screen boundary has not been reached then the routine continues from block 604.

FIG. 10 is a flowchart illustrating the timer interrupt service routine for ECG and heart rate display. This routine is executed periodically as determined by a hardware time which causes an interrupt, typically every three milliseconds.

The routine starts at block 700. At block 701 the signal memory printer is incremented by one. Next the A/D converter is read (block 702) to sample the ECG. The acquired data is then filtered by a digital notch filter to remove the 50 Hz and 60 Hz mains supply interference (block 703). The data is then analyzed to detect the QRS waveform if present for heart rate measurement (block 704). This is further described in FIG. 11.

If the measured signal is outside the display boundary then it is clamped (block 705). The measured signal is then saved in memory (block 706). Next the scan/hold switch 37 is checked and debounced (block 707). If a valid switch push is detected (block 708) then the scan/hold flag is updated (block 709) and then the interrupt routine is terminated (block 710). If no switch push is detected at block 708 then the interrupt routine is terminated immediately at block 710.

Figure 11:
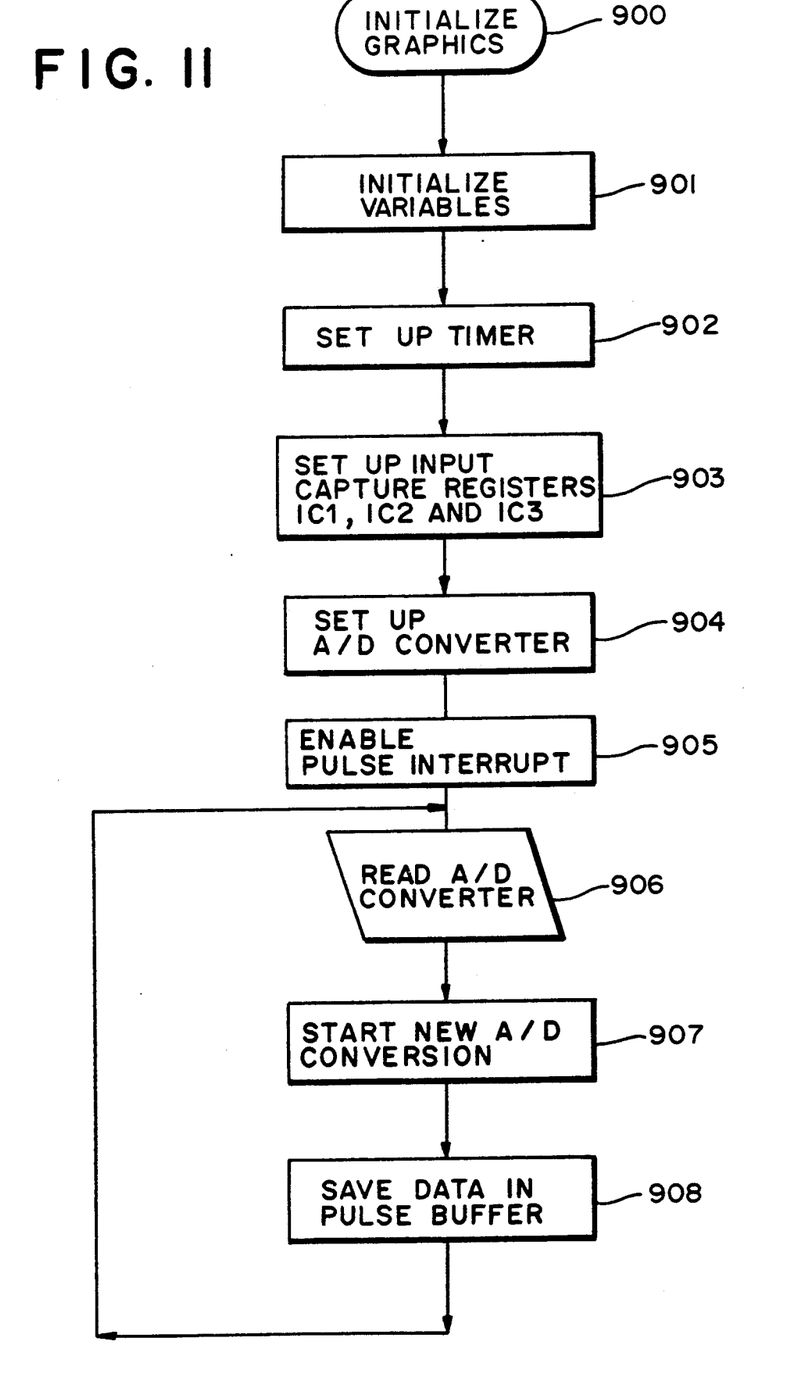
FIG. 11 is the flow chart of the main routine for the pacemaker pulse display algorithm of the third embodiment.

FIG. 11 is a flowchart illustrating the QRS detection algorithm for ECG and heart rate display. The routine starts at block 800. If the QRS flag is not set (block 801), then it is checked to determine whether the refractory period is still set (block 802). If not, the slope of the acquired ECG data is measured (block 803), the polarity of the slope determined (block 8040, and the slope is checked to see if it lies between two thresholds (block 805). If so, the time duration for which the slope has met the other criteria is checked (block 806), and if this duration exceeds a certain limit, the QRS flag is set (block 807), and the thresholds are adjusted (block 808). The routine then terminates at block 809.

If at block 802 the refractory period is still set, then the routine terminates immediately at block 809.

If the threshold criteria at block 805 are not met, then the routine also terminates immediately at block 809.

If the QRS flag is set at block 801, the heart rate calculation is updated. The print inflection of the QRS waveform is checked at block 810. If it is found, then the R-peak has been detected (block 811). The time between successive R-peaks is then calculated and from this the 4-beat running average heart rate is calculated (block 812). The QRS flag is then cleared (block 813) and the routine terminates at block 809.

If, at block 810, the point of inflection is not found, then the routine terminates immediately at block 809.

FIG. 12 is a flowchart illustrating the main routine for pacemaker pulse display. This routine runs continuously, sampling the input signals to capture the pacemaker pulse waveform in memory for measurement and display.

The routine starts at block 900 where the graphics are initialized, followed by block 901 where the variables are initialized. Next the timer is set up (block 902) and the input capture registers IC1, IC2 and IC3 are set up (block 903).

The A/D converter is then set up in block 904 to continuously sample the incoming signal. The hardware pulse interrupt is then enabled to enable the pacemaker pulse edges to be detected (block 905).

The A/D converter is then read (block 906) and new A/D conversion started immediately (block 907). The data read from the A/D converter is then saved in the pulse buffer (block 908) and the program then loops back to read the A/D converter at block 906.

FIG. 13 is a flowchart illustrating the pulse interrupt service routine for pacemaker pulse display. This routine is entered by a hardware interrupt caused by the detection of a pacemaker pulse edge. The purpose of the routine is to validate the detection of a pacemaker pulse to measure the pacemaker pulse parameters, being the pulsewidths, the AV interval and pacing rate, and to display the pacemaker pulse waveform shape and the pacemaker pulse parameters.

The routine begins at block 400 when a hardware pulse interrupt occurs to disable the input capture registers to prevent further interrupts. At block 401, the IC1 and IC2 flags are checked to make sure they are both set. If so, the IC1 and IC2 register values are saved (block 402). Next IC1 is checked to see if it is less than IC2 (block 403). If so, then the start time of the pulse is the value of the IC1 register block 404) and the end time of the pulse is the value of the IC2 register (block 405). If IC1 is not less than IC2 (at block 403) then the order is reversed (blocks 406 and 407).

The pulse width is then calculated by subtracting the IC2 register value from the IC1 register value (block 408).

The pulse width is then checked to determine if it is less than 3 ms (block 409). If it is not, then it is determined not to be a value pulse and the routine ends. If the pulse width is less than 3 ms, then the pulse width is saved (block 410), as well as the pulse arrival time (block 411).

At block 412 a check is made to determine whether three consecutive pulses have been detected. If not, the routine then ends. If so, then further pulse parameters can be measured.

By looking at the timing of the three pulses a determination is made whether the pacemaker is a single or dual chamber pacemaker (block 413).

If it is a dual chamber pacemaker, then the AV interval is calculated (block 4140, and the artial pulse width and pulse shape (block 415), the ventricular pulse width and pulse shape (block 416) and the AV interval (block 417) are all displayed.

Pulse interrupts are then reenabled by enabling the input capture registers (block 419). The interrupt service routine is then terminated (block 420).

If at block 413 it is determined that there is single chamber pacing, only a single pulse width and pulse shape are displayed (block 418) before the routine terminates.

The performance characteristics of the monitor of the third embodiment are as follows:

| | |
|---|---|
| ECG Circuit | |
| Frequency Response: | 0.5–100 Hz (−3dB max) |
| CMMR: | u 80 dB 0–100 Hz |
| Isolation: | Infrared external output |
| Pacemaker Artifact: | Pulse re-insertion |
| Display | |
| Sweep Speed: | 12.5 mm/sec (for ECG) |
| Viewing Area: | 38.1 × 50.8 mm |
| No. of Pixels: | 57,600 (120 × 480) |
| Display Element: | TN type LCD |
| Element Shape: | Trapezoidal |
| Back Light: | Electroluminescent |
| Measured Parameters | |
| Heart Rate (HR): | 0–255 bpm (+1 bpm) |
| Pacemaker Rate (PR): | 0–255 bpm (+1 bpm) |
| A-V Delay Interval (AVI): | 1–300 ms (+1 ms) |
| Atrial Pulse Width (APW): | 0.1–2.5 ms (+5 ms) |
| Ventricular Pulse Width (VPW): | 0.1–2.5 ms (+5 ms) |
| Displayed Parameters | |
| Atrial Pulse Wave Form: | Accuracy of +5 ms |

| -continued | |
|---|---|
| Ventricular Pulse Wave Form: | Accuracy of −5 ms |
| Calibration: | 1 mV/cm square wave |
| ECG wave form: | Sweep speed 12.5 mm/sec |
| Power Requirements | |
| Battery Type: | 2 × AA Alkaline cells |
| Battery Life: | u 4 hours continuous use |
| Physical Characteristics | |
| Length: | 13.4 cm |
| Width: | 8.5 cm |
| Thickness: | 2.6 cm |
| Weight: | 410 gm |
| Environmental Characteristics | |
| 5.3.1 Temperature | |
| Operating: | 5° to 45° C. |
| Storage: | −15° to 55° C. |
| 5.3.2 Humidity | |
| Operating: | 10% to 95% |
| Storage: | 10% to 80% |

The functional behavior of the monitor of the second embodiment with reference to the controls and display previously described are as follows:

OPERATOR CONTROLS

On/Off

When switch 39 is switched to the ON position the ECG monitor mode is invoked. In the OFF position all operation modes are powered down, with the exception of the data in memory which is retained until the system is reset manually or by output to a printer or computer.

Contrast

A potentiometer 40 is used to control the contrast level to the LCD 31.

Hold

A momentary push button 36 that causes the current display to be frozen. No data update occurs at this time.

Record

A momentary push button 37 that initiates the recording of the current displayed data for a 10 second interval. There are six intervals available for recording. At the commencement of the recording a 1 mV calibration signal is displayed.

Mode

A momentary push button 38 that toggles between the ECG/heart rate display and the pacemaker wave forms and data display. (Refer FIGS. 2A and 2B.)

Reset

By depressing MODE 38 and RECORD 37 buttons simultaneously the recording memory is reset, clearing all previously recorded data.

INDICATORS

Heart Rate (HR)

The heart rate is indicated on the LCD 6 (display 1 of FIG. 2A) and determined by using a four beat running average of the R to R interval.

Pacemaker Rate (PR)

The pacemaker rate is indicated separately on the LCD 31 and represents the actual pacing rate. Should there not be "capture" the paced rate as well as the heart rate will be displayed.

Atrio-Ventricular Delay Interval (AVI)

The A-V delay is measured in milliseconds and displayed 7 on the pacemaker data screen.

Atrial Pulse Width (APW)

The atrial pulse width is measured and displayed 8 when an atrial pulse is present. In addition the atrial wave form 5 is displayed.

Ventricular Pulse Width (VPW)

The ventricular pulse width is measured and displayed 9 when a ventricular pulse is present. In addition the ventricular waveform is displayed 10.

Low Battery

Should the operational voltage drop below an optimal level a continuous audible tone is sounded for 1 second. At this time the procedure should be completed as soon as possible and batteries replaced or re-charged.

Functional Test

The monitor becomes operational in the ECG monitor mode when the power switch is turned ON. At this time at test cycle of 1 second is initiated to check the microprocessor function, memory integrity, and display characteristics, with a separate battery voltage check. On completion of the test cycle a 1 second audible tone is sounded to indicate correct functional operation.

Calibrate

At the RECORD button being depressed a 1 mV calibration pulse is inserted initially to allow accurate wave form analysis.

INPUT/OUTPUT CONNECTORS

Patient Cable Input

The patient cable input is a Lemo Series "OB" fixed socket connector. It has three inputs RA, LA and RL to obtain the ECG/pacemaker signals.

Infrared Output Link

The infrared output 42 is a bi-directional communications link. This output provides total electrical isolation when connected to external devices, such as printers, computers or serial communications links.

In summary, the monitor of the second embodiment behaves as previously described within the following limits.

Pacemaker parameters are measured by detecting the pacing pulse artifacts on the skin surface, then amplifying and filtering them and converting them to digital signals for analysis by the CPU 57 of the second embodiment.

The digital hardware and software is capable of resolving pacing pulse widths down to 1 us with a resolution of +/−0.5 us. The AV display and pacing rate can be resolved to +/−128 us, though with software changes this can be reduced to +/−0.5 us.

The actual resolution of the pacing pulse widths is governed by the analog circuitry. Two factors are important here. Slew rate limitations of the amplifiers mean that there may be an error of 1 us. The second factor is really one of the definition of pacing pulse width. Pacemaker manufacturers may define the pulse width at a different level on the pulse compared with the monitor of the second embodiment and may also measure them in vitro. Depending on the characteristics of the pulse, this may amount to an error of up to 5 us when compared with the published specification of the pacemaker.

Taking all these factors into account, the monitor of the second embodiment can satisfactorily measure pacing pulse widths down to 10 us if required with a resolution of +/−1 us, though measurement may vary in some cases by up to 5 us from pacemaker published data due to a difference in measurement technique between the monitor and the pacemaker manufacturer. AV delays and pacing rates have a resolution of +/−128 us.

Importantly too the onboard memory storage of the device combined with the option to actually store data derived by the monitor within the monitor casing allows a medical practitioner to take the monitor of either the first or the second embodiment into the field and take "samples" of a patient's ECG and pacemaker wave form behaviour for subsequent analysis in the office. Similarly, a patient can be supplied with a monitor and instructed to take samples of the patient's own wave forms him or herself at predetermined times each day or during or following specific "events". The whole monitor can then be given to the practitioner at a later time at which time the practitioner can recall the stored data and analyze it.

The above describes three embodiments of the present invention and modifications, obvious to those skilled in the art, can be made thereto without departing from the scope and spirit of the present invention.

For example, the infrared link 42 can be replaced by a RF radio link or an ultrasonic communications link. In all cases the purpose of the link is to provide a wire free means of communicating data derived by the monitor of the invention to remote data processing and/or recording means and/or hard copy means to allow subsequent and/or concurrent display and analysis of a patient's ECG and pacemaker wave forms and, most importantly, the interaction between those two wave forms.

We claim:

1. A portable, handheld monitor for monitoring and displaying simultaneously pacemaker parameter information and vital sign parameter information, said monitor comprising:

a housing of a size and shape that can be easily held in a user's hand;

data acquisition means mounted on the housing for receiving electrical signals from a skin contact region of a patient, the electrical signals being representative of pacemaker parameters including a pacemaker pulse waveform and at least one from parameters including pulse rate, pulse width, pulse interval, AV interval, or Atrial and Ventricular pulse discrimination and said electrical signals further being representative of vital sign parameters including at least heart rate and ECG wave forms;

data processing means provided within the housing and coupled to the data acquisition means for processing said electrical signals and producing pacemaker parameter information including at least pacemaker pulse timing markers and vital sign parameter information including ECG waveform information and heart rate information therefrom;

LCD display means mounted within said housing and coupled to said data processing means for displaying said pacemaker parameter information and said vital signal parameter information simultaneously; and means to superimpose said ECG waveform information and said timing markers on said LCD display means so that relative timing information can be observed by an observer of said display means.

2. A monitor as claimed in claim 1 wherein the data processing means further includes means to process the electrical signals representative of the pacemaker pulse waveform to produce pacemaker pulse waveform shapes, and the display means displays the waveform shapes.

3. A monitor as claimed in claim 1 wherein said data acquisition means comprises a plurality of electrodes for placing on said skin contact region for picking up said electrical signals representative of said pacemaker parameters.

4. A monitor as claimed in claim 1 further comprising memory means for storing data corresponding to said electrical signals, said vital sign parameter information and said pacemaker parameter information, the stored data being available for subsequent recall and display or transmission to remote data processing means.

5. A monitor as claimed in claim 4 further comprising transmission means for transmitting said stored data, said electrical signals, said vital sign parameter information and said pacemaker parameter information to remote data processing means.

6. A monitor as claimed in claim 5 wherein said transmission means comprises an infrared transmitter.

7. A monitor as claimed in claim 5 wherein said transmission means comprises a radio frequency transmitter.

8. A monitor as claimed in claim 5 wherein said transmission means comprises an ultrasonic transmitter.

9. A monitor as claimed in claim 1, wherein said data processing means including means to differentiate between atrial pacemaker pulses and ventricular pacemaker pulses and to determine the interval therebetween, and the display means further includes means to display a measurement of the interval between the atrial and the ventricular pacemaker pulses.

10. A method of monitoring and displaying simultaneously vital sign parameter information and pacemaker pulse parameter information on a single LCD display means, said method comprising the steps of:
sensing electrical signals from a skin contact region of a patient in real time, the electrical signals being representative of pacemaker parameters including pacemaker pulse waveform and at least one from parameters including pulse rate, pulse width, pulse interval, AV pulse interval, or Atrial and Ventricular pulse discrimination of pacemaker heart stimulation pulses produced by a pacemaker operating with said patient and vital sign parameters including at least heart rate and ECG waveforms occurring in said patient;
processing said electrical signals representative of pacemaker parameters to produce pacemaker parameter information including at least pacemaker pulse timing markers therefrom;
processing said electrical signals representative of vital sign parameters to produce vital sign parameter information including ECG waveform information and heart rate information therefrom; and
displaying on said single LCD display means at least said pacemaker pulse timing markers superimposed on the ECG waveform that relative timing information can be observed by an observer of said display means.

11. The method of claim 10 further comprising the steps of:
processing the electrical signals representative of the pacemaker pulse waveform to reconstruct the pacemaker pulses; and
displaying said reconstructed pacemaker pulses.

12. The method of claim 11, wherein the step of processing the electrical signals includes processing said signals so that said reconstructed pacemaker pulses are an approximation of the actual pulse shape of each of said pacemaker pulses.

13. A portable, handheld monitor for monitoring and displaying simultaneously pacemaker parameter information and vital sign parameter information, said monitor comprising:
a housing of a size and shape than can be easily held in a user's hand;
data acquisition means mounted on the housing for receiving electrical signals from a skin contact region of a patient, the electrical signals being representative of pacemakers including pacemaker pulse waveform and at least one from parameters including pulse rate, pulse width, pulse interval, AV interval, or Atrial and Ventricular pulse discrimination, said electrical signals further being representative of vital sign parameters including at least heart rate and ECG wave forms;
data processing means provided within the housing and coupled to the data acquisition means for processing said electrical signals and producing pacemaker parameter information including at least pacemaker pulse timing markers and vital sign parameter information including ECG waveform information and heart rate information therefrom, said data processing means including
a) amplifier means for receiving said electrical signals from said data acquisition means and producing an amplified data signal,
b) first circuit means including low pass filter means responsive to said data signal for producing ECG signals corresponding to said ECG waveforms,
c) second circuit means including divider means and high pass filter means responsive to said data signal for producing pacemaker signals corresponding to said pacemaker pulse waveform, and
d) third circuit means including a high pass filter and threshold comparator means for producing pulse timing markers,
LCD display means mounted within said housing and coupled to said data processing means for displaying said pacemaker parameter information and said vital signal parameter information simultaneously; and
graphic control means to supply said pulse tuning markers and said ECG waveform to said LCD display means so as to superimpose said ECG waveform and said timing markers on said LCD display means so that relative timing information can be observed by an observer of said display means.

* * * * *